US006254833B1

(12) United States Patent
Shumate et al.

(10) Patent No.: US 6,254,833 B1
(45) Date of Patent: Jul. 3, 2001

(54) MICROPLATE LID

(75) Inventors: Christopher B. Shumate, La Jolla; Peter J. Coassin, Encinitas, both of CA (US)

(73) Assignee: Aurora Biosciences Corporation, San Diego, CA (US)

( * ) Notice: Subject to any disclaimer, the term of this patent is extended or adjusted under 35 U.S.C. 154(b) by 0 days.

(21) Appl. No.: 09/134,662

(22) Filed: Jul. 30, 1998

Related U.S. Application Data

(63) Continuation-in-part of application No. 09/030,578, filed on Feb. 24, 1998, now Pat. No. 6,171,780, which is a continuation-in-part of application No. 09/028,283, filed on Feb. 24, 1998, now abandoned.

(51) Int. Cl.[7] .................................................. B01L 3/00
(52) U.S. Cl. ........................... 422/102; 422/99; 435/298; 435/300; 206/503
(58) Field of Search ................................ 422/101, 102, 422/297, 300, 99; 435/305.3, 305.4, 298, 287; 206/503, 508, 557, 565, 821

(56) References Cited

U.S. PATENT DOCUMENTS

| D. 269,702 | 7/1983 | Suovaniemi et al. . |
| D. 288,604 | 3/1987 | Winston et al. . |
| D. 317,360 | 6/1991 | Gabridge . |

(List continued on next page.)

FOREIGN PATENT DOCUMENTS

| WO 86/07606 | 12/1986 | (WO) . |
| WO 92/01513 | 2/1992 | (WO) . |
| WO 92/01553 | 2/1992 | (WO) . |
| WO 95/22406 | 8/1995 | (WO) . |
| WO 96/39481 | 12/1996 | (WO) . |
| WO 97/00136 | 1/1997 | (WO) . |
| WO 97/12678 | 4/1997 | (WO) . |
| WO 98/38490 | 9/1998 | (WO) . |
| WO 98/41874 | 9/1998 | (WO) . |
| WO 98/42442 | 10/1998 | (WO) . |
| WO 98/46981 | 10/1998 | (WO) . |

OTHER PUBLICATIONS

"Working Group Udates", Astle, Journal of Biomolecular Screening, vol. 1, No. 4, 1996, pp. 163–168.
Corning Costar 1996/1997 Catalog *No month available.
Corning Costar "High Throughput Screening" Catalog * No date available.
Corning Costar PCR Reaction Vessels *No date available.
Corning Costar 96 Well UV–Plate *No date available.
Corning Costar 1995 Product Selection Guide * No month available.
Corning Costar 96 Well Assay Block *1997, No month available.
Corning Costar Corporation, "The HTS Forum", vol. 1, Aug. 1997.
Corning Costar 384 Well Plates Catalog, "Turn Down the Volume Turn Up the Productivity" *No date available.
VWR Scientific Products 1997/1998 Catalog *No month available.
NUNC FluoroNunc™ Advertisement *No date available.
NUNC™ Products 1996 Catalog *No month available.
Millipore 1997 Laboratory Catalogue *No month available.
Greiner Labrotechnik Micro–Assay Plate, 1536 wells Catalog *No date available.

*Primary Examiner*—Kathryn Gorgos
*Assistant Examiner*—Dwayne K. Handy
(74) *Attorney, Agent, or Firm*—Gray Cary Ware & Freidenrich LLP; Lisa A. Haile

(57) ABSTRACT

A microplate lid having a substantially flat, generally rectangular top with first and second pairs of opposite sides. A flange depends from the top of the first and second pairs of sides, the flange bearing at least one recess area along each side of the first pair of sides, the recessed area extending into the top.

7 Claims, 6 Drawing Sheets

U.S. PATENT DOCUMENTS

| | | |
|---|---|---|
| 4,004,150 | 1/1977 | Natelson . |
| 4,038,149 * | 7/1977 | Liner et al. ............................ 195/127 |
| 4,105,325 | 8/1978 | McCollough . |
| 4,154,795 | 5/1979 | Thorne . |
| 4,251,159 | 2/1981 | White . |
| 4,271,270 * | 6/1981 | Lukascek ............................ 435/294 |
| 4,545,958 | 10/1985 | Dopatka . |
| 4,735,778 | 4/1988 | Maruyama et al. . |
| 4,770,856 | 9/1988 | Uthemann et al. . |
| 4,797,259 | 1/1989 | Matkovich et al. . |
| 4,828,386 | 5/1989 | Matkovich et al. . |
| 4,892,409 | 1/1990 | Smith . |
| 4,948,442 | 8/1990 | Manns . |
| 5,047,215 | 9/1991 | Manns . |
| 5,083,666 * | 1/1992 | Lam ...................................... 205/506 |
| 5,084,246 | 1/1992 | Lyman et al. . |
| 5,110,556 | 5/1992 | Lyman et al. . |
| 5,147,780 | 9/1992 | Pouletty et al. . |
| 5,154,315 | 10/1992 | Dominico et al. . |
| 5,225,164 | 7/1993 | Astle . |
| 5,234,665 | 8/1993 | Ohta et al. . |
| 5,294,795 | 3/1994 | Lehtinen et al. . |
| 5,319,436 | 6/1994 | Manns et al. . |
| 5,419,451 * | 5/1995 | Bitel, Jr. ................................ 220/306 |
| 5,456,360 | 10/1995 | Griffin . |
| 5,457,527 | 10/1995 | Manns et al. . |
| 5,487,872 | 1/1996 | Hafeman et al. . |
| 5,507,085 | 4/1996 | Easton et al. . |
| 5,516,490 | 5/1996 | Sanadi . |
| 5,547,081 * | 8/1996 | Mullock et al. ...................... 206/504 |
| 5,587,321 * | 12/1996 | Smith et al. ........................ 435/305.3 |
| 5,604,130 | 2/1997 | Warner et al. . |
| 5,609,826 | 3/1997 | Cargill et al. . |
| 5,679,310 | 10/1997 | Manns . |
| 5,682,232 | 10/1997 | Tajima et al. . |
| 5,741,463 | 4/1998 | Sanadi . |
| 5,759,494 | 6/1998 | Szlosek . |
| 5,789,251 | 8/1998 | Astle . |
| 5,858,309 | 1/1999 | Mathus et al. . |
| 5,882,922 * | 3/1999 | Tyndorf et al. .................... 435/305.3 |

* cited by examiner

MICROPLATE LID

The present application claims the benefit of the filing date of the following applications: C-I-P U.S. patent application Ser. No. 09/030,578, filed Feb. 24, 1998, now U.S. Pat. No. 6,171,780; and a C-I-P U.S. patent application Ser. No. 09/028,283, filed Feb. 24, 1998, now abandoned; each of which are incorporated herein by reference.

BACKGROUND

This invention relates to the field of biomedical testing, and more particularly to the transport, handling and processing of biomedical sample holders such as microplates. Microtiter plates, commonly known as "microplates", facilitate the simultaneous testing (or other processing) of a large number of individual biomedical samples. Microplates have been in common use for decades with a predominant format being a molded plastic plate having 96 sample wells in an 8×12 rectangular array. Typical well volumes are 200 or 300 microliters, depending upon the manufacturer and model of plate, although other volumes may be provided for specific uses. A proposed standard, designated "Microplate 96-Well Standard" (MP96) has been promulgated by The Society for Biomolecular Screening, as published in *Journal of Biomolecular Screening,* Volume 1, Number 4, 1996, the disclosure of which is incorporated herein by reference. A microplate which meets the general dimensional requirements of the standard is designated MP96-3. Typically, each microplate manufacturer will also provide a compatible lid. A typical lid comprises a generally rectangular flat planar top surrounded by a flange depending from the top along its sides and edges.

Automated handling of microplates has become an important criterion in their design. It is therefore desirable to provide a microplate lid configuration that facilitates use with automation. Specifically, it is desirable to provide a lid that facilitates automatic stacking and unstacking of lidded microplates, automatic stacking and unstacking of lids without microplates, and automated installation and removal of lids from microplates.

SUMMARY

In one embodiment, the invention is directed to a lid which is the unitarily formed combination of a substantially flat, generally rectangular top having first and second pairs of opposite sides and a flange, depending from the top along the first and second pair of sides, the flange bearing at least one recessed area along each of the first pair of sides, the recessed area extending into the top.

Some implementations may include one or more of the following: (1) each side of the first pair of sides may have two such recessed areas; (2) each side of the second pair of sides may have at least one recessed area extending toward the top; (3) each side of the second pair of sides may have one recessed area extending toward but not reaching the top.

In one embodiment, the flange may bear two recessed areas along each of the first pair of sides extending into the top and two recessed areas along each of the second pair of sides extending into the top, with a third recessed area along each of the second pair of sides, between the two recessed areas that extend into the top on such sides, but not reaching the top. The three recessed areas of each of the second pair of sides may be contiguous and the third recessed area may have a substantially straight leading edge. The lid may have a sealing feature for sealing to the top of the microplate and the sealing feature may comprise a substantially continuous lip depending from the lower surface of the top slightly inboard of the sides and uninterrupted by any of the recesses.

A further embodiment of the invention is directed to a process for adding to and removing from a stack of lidded microplates. The initial lowermost microplate in the stack is supported at a first height by a pair of opposite, inwardly-directed support features of a stacking/unstacking machine, each remaining microplate in the stack resting atop the lid of the microplate immediately below. The process may include the steps of adding an additional microplate to the stack as a new lowermost microplate by elevating the additional microplate with an elevator from below the stack until the lid supports the initial lowermost microplate, the support features being accommodated by a pair of opposite, inwardly-directed recesses in the lid of the additional microplate. The support features are separated to allow passage of the additional microplate and the additional microplate is further elevated until it reaches at least the first height, whereupon the support features may be inserted beneath the additional microplate and the elevator lowered so as to disengage the elevator from the stack, leaving the stack supported by the support features and leaving the additional microplate as the new lowermost in the stack. The process may be repeated with further microplates added to the stack in place of the new lowermost microplate.

The invention may further provide for the removal of a microplate from the stack by raising an elevator to engage the lowermost microplate, further raising the elevator to disengage the stack from the support features, separating the support features and lowering the elevator. The support features may be reinserted so that they are accommodated by a pair of opposite, inwardly-directed recesses in the lid of the lowermost microplate and the elevator further lowered so that the microplate above the lowermost microplate is engaged by the support features and becomes the new lowermost microplate as the previous lowermost microplate may be removed.

In a further embodiment, the invention provides for removing a microplate lid by introducing a pair of stop features to a pair of opposite, inwardly-directed recesses in the lid of the microplate so at least a portion of the stop features are positioned directly over at least a portion for the microplate. The lid may be raised with the stop members preventing movement of the microplate so as to permit separation of the lid from the microplate. The raising of the lid may comprise introducing a pair of lifting features into a pair of opposite, inwardly-directed recesses in the lid with at least a portion of the lifting features extending immediately below a portion of the lid.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference numbers and designations in the various drawings indicate like elements.

DETAILED DESCRIPTION

Figure 1:
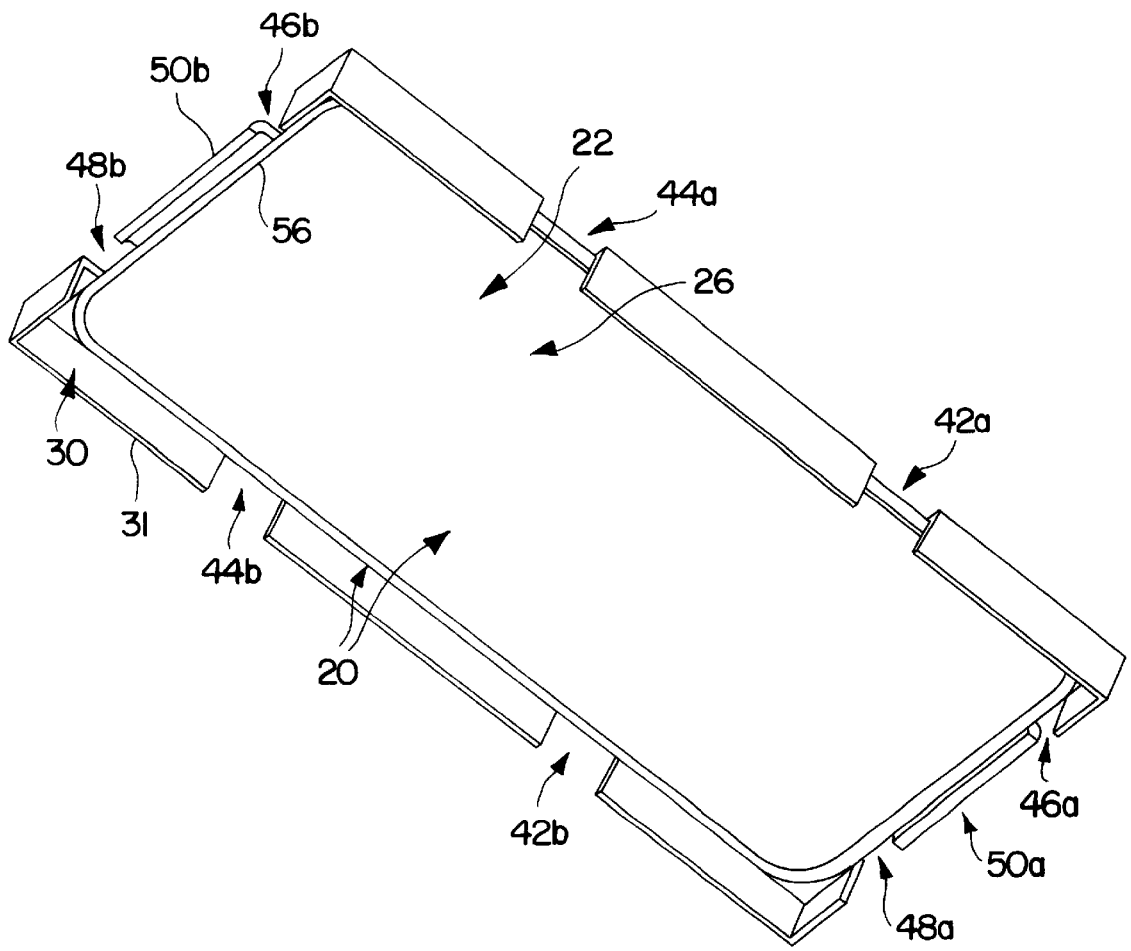
FIG. 1 is a perspective view of a lid according to principles of the invention.
Figure 2:
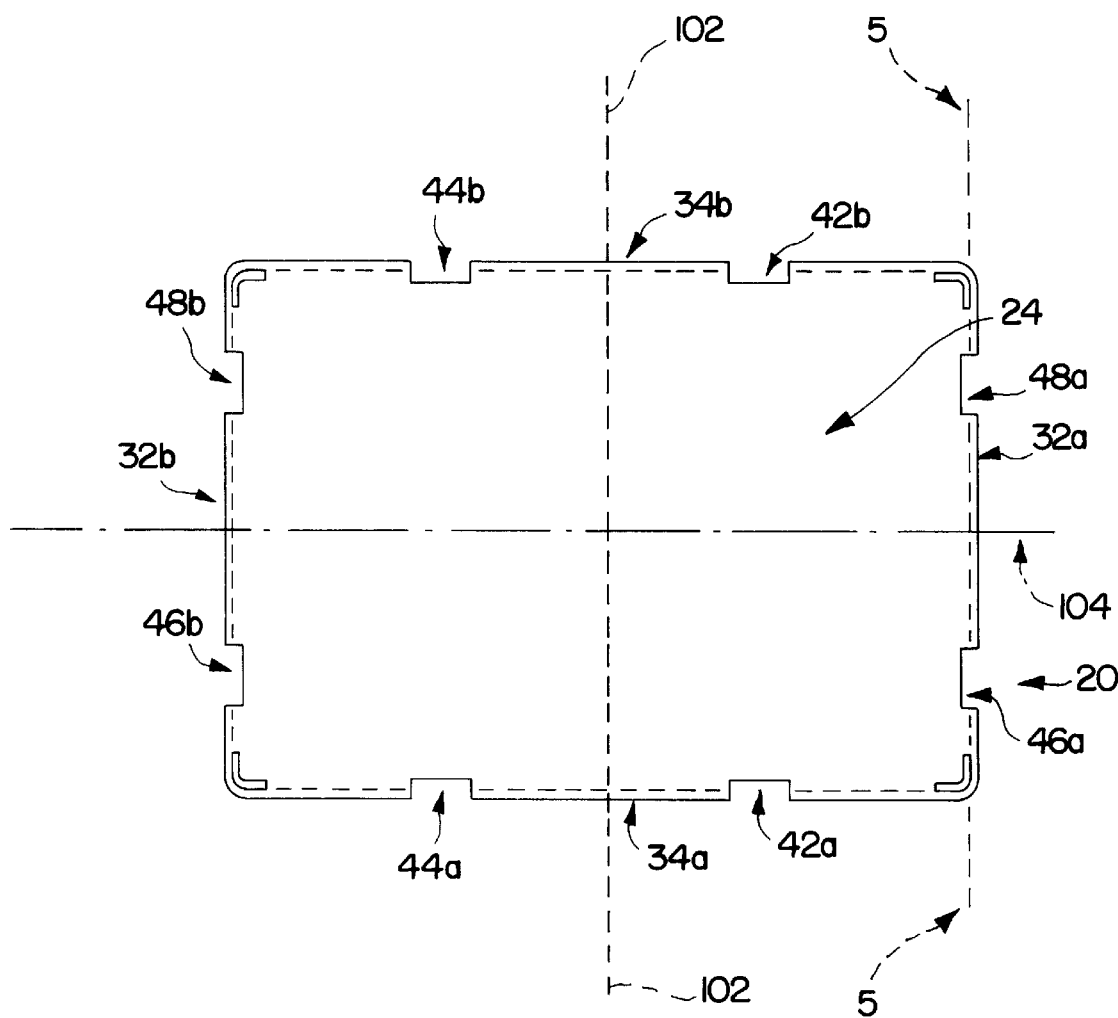
FIG. 2 is a top view of the lid of FIG. 1.

One embodiment of a microplate lid according to principles of the invention is shown in FIG. 1. The materials for manufacturing the lid will typically be polymeric, since these materials lend themselves to mass manufacturing techniques, for example polystyrene or a cycloolefin polymer. However, other materials can be used such as glass or quartz. Preferably, polymers are selected that have low fluorescence and or reflectance. Additionally materials such as polymers can include pigments to darken the lid and absorb light. Such application of pigments will help reduce background fluorescence. Pigments can be introduced by any means known in the art, such as coating or mixing during the manufacture of the material or multi-well platform. Pigment selection can be based on a mixture of pigments to dampen all background inherent to the polymer, or a single pigment or ensemble of pigments selected to filter or absorb light at desired wavelengths. The lid 20 comprises a generally rectangular top 22 preferably having planar upper and lower surfaces 24 FIG. 2 and 26, respectively. A flange 30 depends from all four sides of the top. For purposes of exposition, the shorter sides are referred to as a pair of front and back ends 32a and 32b, and the longer sides as left and right sides 34a and 34b, respectively. With the exception of the presence of recesses (described below), the flange 30 continuously surrounds the top in the preferred embodiment.

Figure 3:
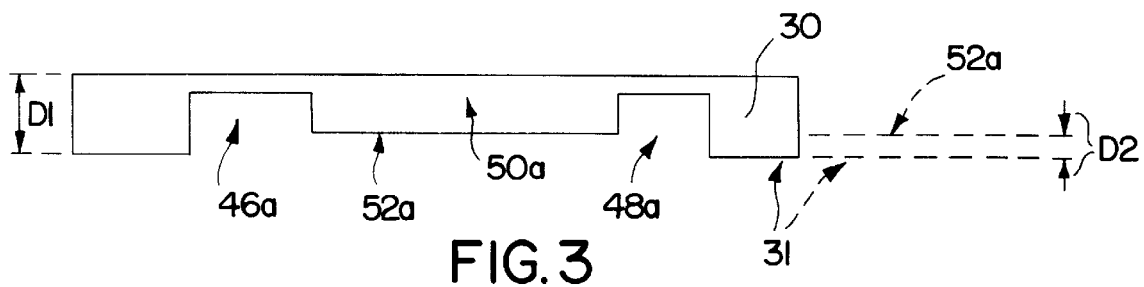
FIG. 3 is an end view of the lid of FIG. 2.
Figure 4:
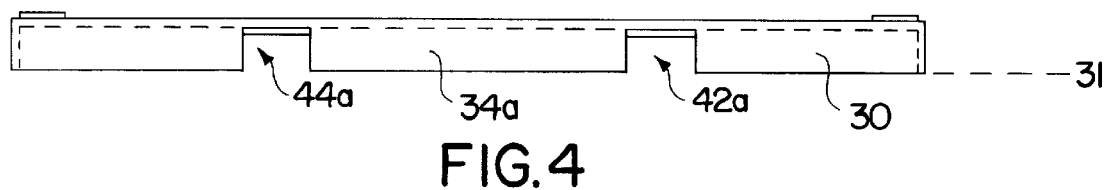
FIG. 4 is a side view of the lid of FIG. 2.

On opposite sides of a transverse centerline 102, the flange bears a recessed area 42a and 44a and 42b and 44b along each side 34a and 34b, respectively, extending toward and slightly into the top. Similarly, on opposite sides of the longitudinal centerline 104, the flange bears a recessed area 46a and 44a and 46b and 48b along each end 32a and 32b, respectively, extending toward and slightly into the top. Along each end 32a and 32b, the flange also bears a slightly recessed area 50a and 50b, respectively, positioned centrally between and connecting recessed areas 46a and 48a and 46b and 48b, respectively FIG. 3. Although recesses 50a and 50b extend slightly toward the tops they do not reach it, having straight leading edges 52a and 52b which are recessed only slightly relative to the leading edge 31 of the remainder of the flange.

In the exemplary embodiment, the general dimensions of the top are approximately 5.03 inches in length between the ends, and 3.25 inches in width between the sides, with a thickness of 0.06 inches. The flange 30 has a depth (D1) of 0.25 inches (from the upper surface of the top to the leading edge 31 of the flange) and the central recessed areas 50a and 50b are recessed by a distance D2 of 0.125 inches from the leading edge 31 of the flange.

Figure 5:
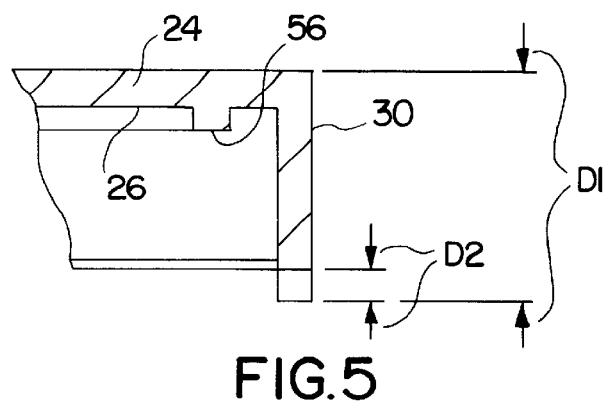
FIG. 5 is a partial cross-sectional view of the lid of FIG. 2, taken along line 5—5.

As shown in FIG. 5, a sealing feature 56 depends from the lower surface or underside 26 of the top 24 and is formed as a substantially continuous lip, located slightly inboard of ends 32a and 32b and sides 34a and 34b and uninterrupted by the recesses. The sealing feature can support the lower surface 26 of the top above the upper surface or top of the microplate and may provide a seal with the microplate. In the exemplary embodiment, the sealing lip extends 0.03 inches below the underside 26 of the top 24.

Figure 6:
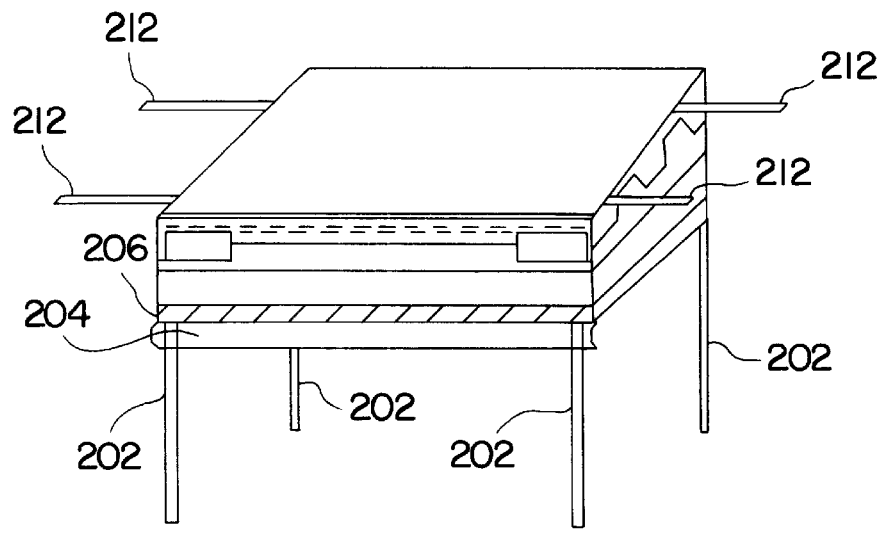
FIG. 6 is a semi-schematic view of a system for stacking and unstacking lidded microplates according to principles of the invention.
Figure 7:
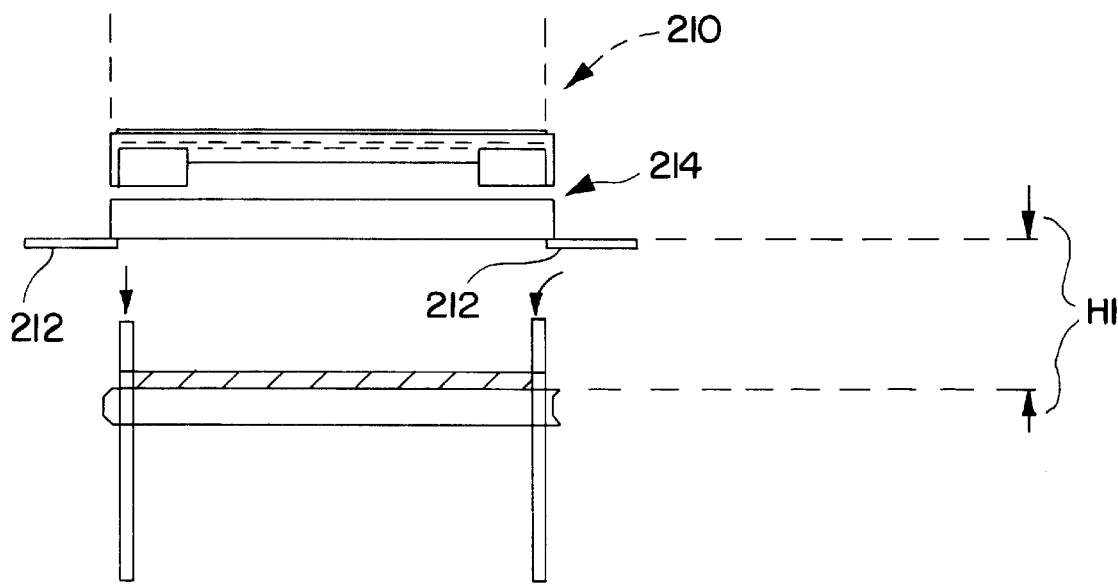
FIGS. 7–10 are semi-schematic views of the stacking system of FIG. 6 in various stages of operation.
Figure 8:
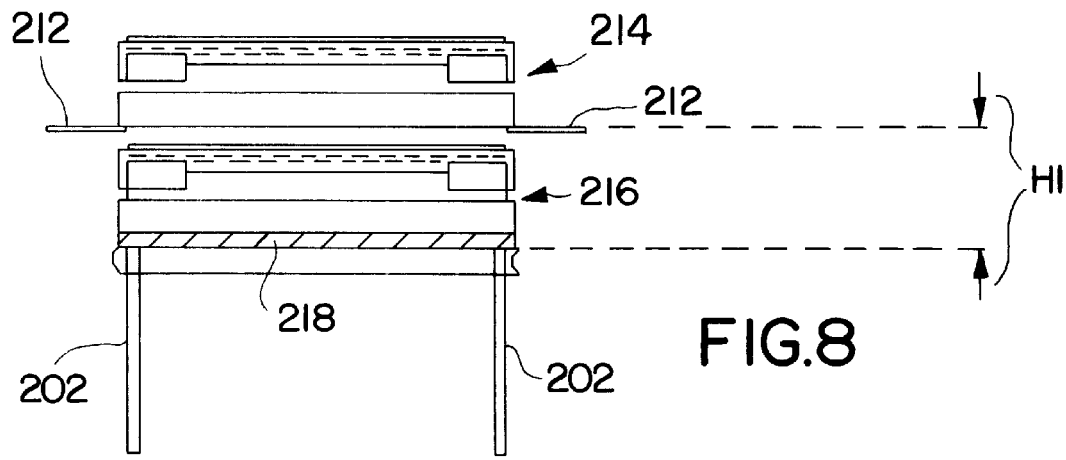
Figure 9:
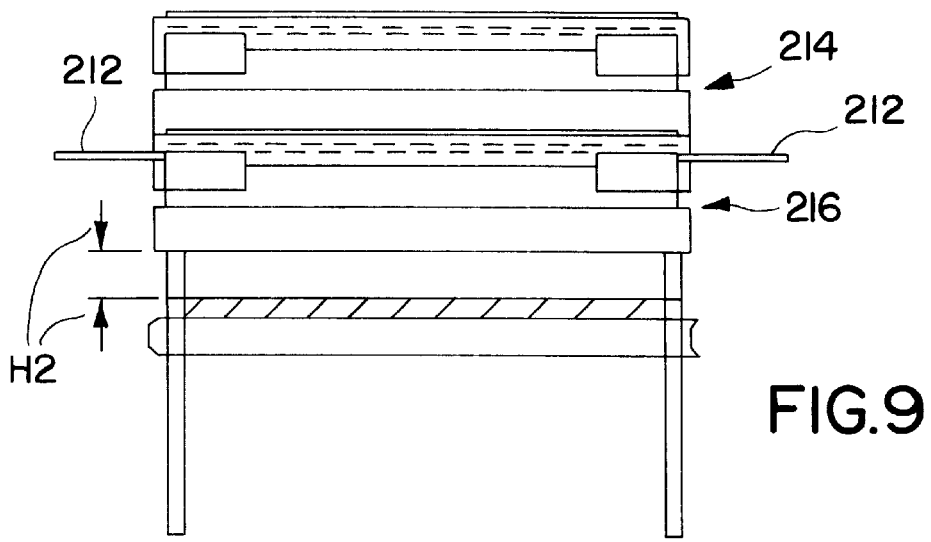
Figure 10:
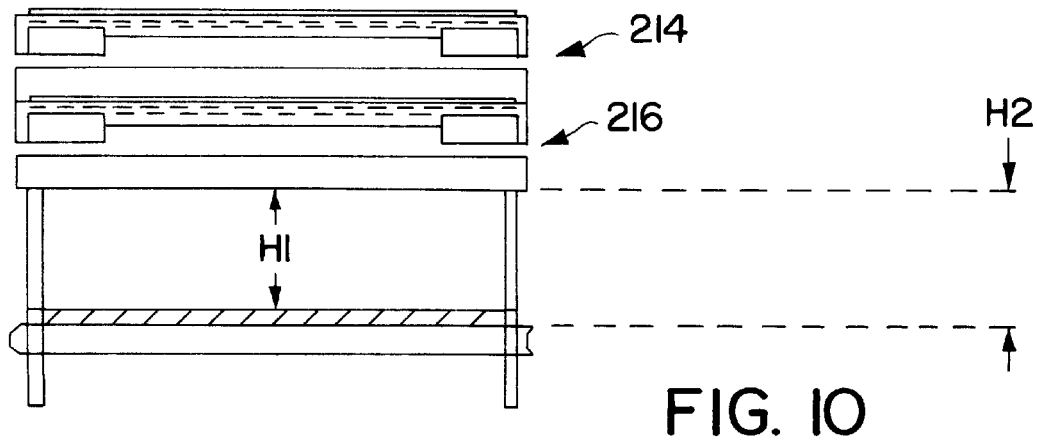

Shown in FIG. 6 is an apparatus for stacking and destacking lidded microplates. The apparatus includes an elevator comprising four threaded lifting shafts 202. Rotation of the shafts will raise or lower the shafts relative to a base 204 so that their upper ends 206 can engage the bottom of a microplate. As further shown in FIG. 7, in an exemplary process for adding to and removing from a stack 210 of lidded microplates, an initial lowermost first microplate 214 is supported at a first height H1 by a pair of opposite, inwardly-directed, support fingers 212. Each remaining microplate in the stack rests atop the lid of the microplate immediately below. As shown in FIGS. 7 and 8, a second lidded microplate 216 (FIG. 8) is brought under the stack such as by means of a conveyor belt 218 around which the shafts 202 are free to pass. The shafts are rotated so that they raise and engage the bottom of the second microplate 216. Further rotation elevates the microplate until its lid supports the first microplate 214, the support fingers being accommodated by the recesses 42a and 42b and 44a and 44b (FIG. 9). The support fingers are then separated to allow passage of the second microplate 216 and the second microplate is further elevated until it reaches a height H2 slightly above height H1 FIG. 10. The support fingers are then reinserted beneath the second microplate and the shafts counter-rotated to descend, and leave the stacks 210 supported at height H1 with the second microplate 216 as the new lowermost microplate. The shafts may then be further lowered to their original position to receive a third microplate and the procedure repeated to make the third microplate a new lowermost microplate in the stack.

The procedure may be substantially reversed to remove the lowermost microplate from the stack. To do this, the shafts are raised until they engage the lowermost microplate 216 at height H1 and then further raised to height H2 to disengage the stack from the support fingers 212 FIG. 10. The support fingers are then separated, allowing the stack to be lowered until the support fingers can be reinserted so that they are accommodated by the recesses in the lid of the lowermost microplate 216 FIG. 9. The shafts may be further lowered so that the support fingers engage the microplate 214 immediately above the lowermost microplate 216, microplate 214 then becoming the current lowermost microplate in the stack. The previous lowermost microplate 216 is then lowered further and may be removed.

Figure 11:
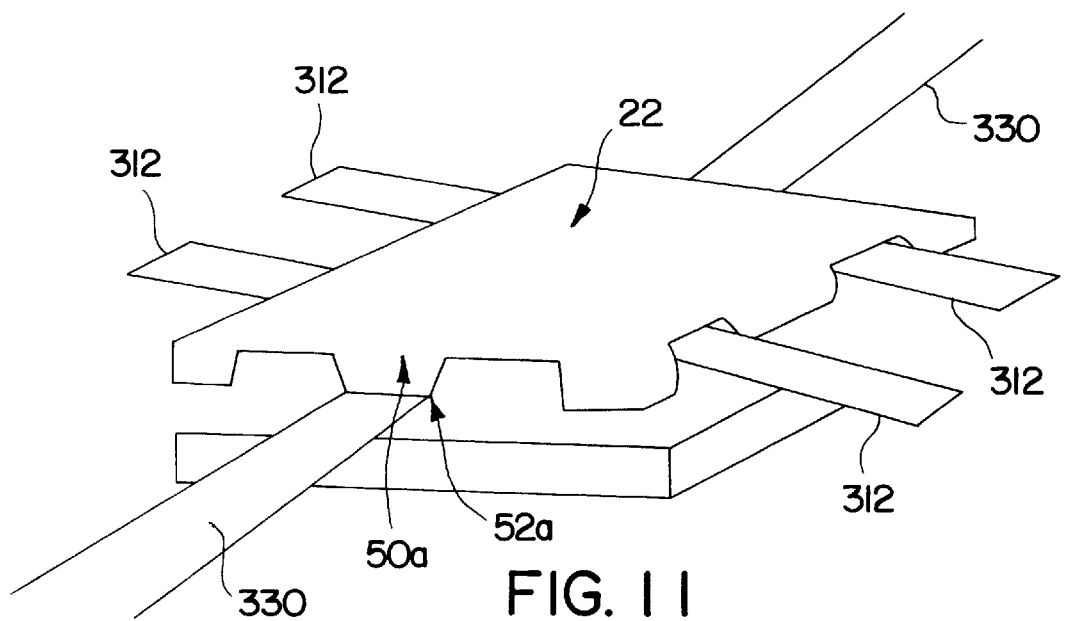
FIGS. 11 & 12 are partial-schematic views of a system for removing lids from microplates according to principles of the invention.
Figure 12:
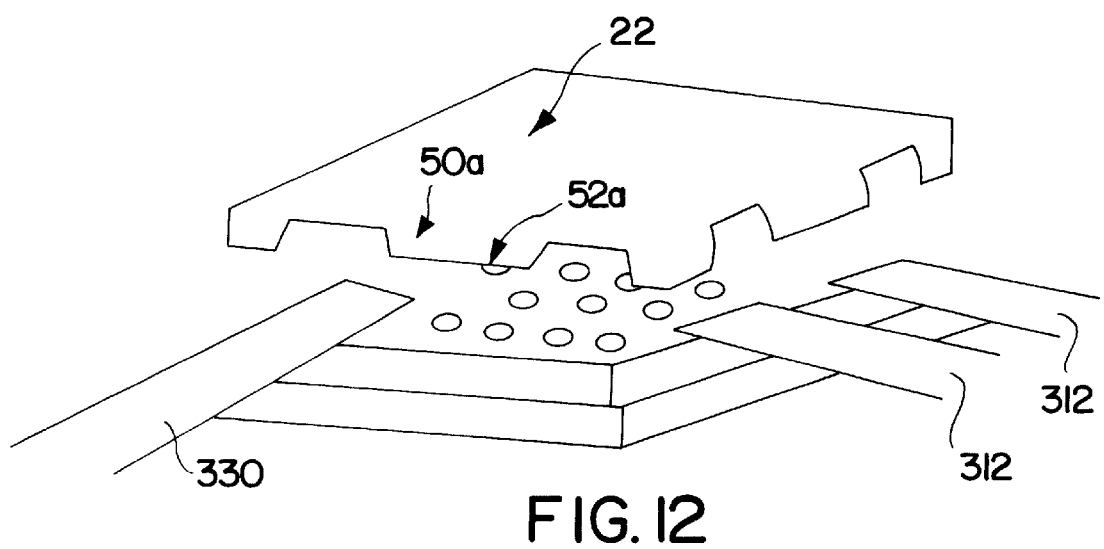

As shown in FIGS. 11 & 12, once the lid of a microplate is free of the stack, the presence of the recesses facilitates automated removal of the lid from the microplate. Pairs of opposite inwardly directed stop fingers 312, which may be otherwise similar to fingers 212, are inserted into the recesses, 42a and 42b and 44a and 44b, so that at least a portion of the fingers are positioned directly above at least a portion of the microplate. A pair of opposite, inwardly-directed, lifting fingers 330 are then inserted into the recesses 50a and 50b so that they come immediately below the leading edges 52a and 52b, respectively.

As shown in FIG. 12, the lifting fingers 330 are raised to engage the leading edges 52a and 52b and raise the lid, with the stop fingers 312 engaging the upper surface of the microplate so as to prevent movement of the microplate and permit separation of the lid from the microplate.

Although various processes have been described as performed relative to the recesses 42a and 42b and 44a and 44b on the sides of the lid, such processes may also be performed relative to the recesses 46a and 46b and 48a and 48b on the ends of the lid.

A number of embodiments of the present invention have been described. Nevertheless, it will be understood that various modifications may be made without departing from the spirit and scope of the invention. For example, although the illustrated recesses on a given side are formed in pairs on opposite sides of the associated center line (and particularly the center of gravity), other configurations such as a bored recesses spanning the center line are similarly useful. Accordingly, other embodiments are within the scope of the following claims.

Publications

All publications, including patent documents and scientific articles, referred to in this application are incorporated by reference in their entirety for all purposes to the same extent as if each individual publication were individually incorporated by reference.

All headings are for the convenience of the reader and should not be used to limit the meaning of the text that follows the heading, unless so specified.

We claim:

1. A lid comprising the unitarily formed combination of:
   (a) a rectangular surface comprising an upper surface and a lower surface having first and second pairs of opposite sides;
   (b) a flange depending from said surface along said first and second pairs of sides, said flange bearing at least one recessed area along each side of said first pair of sides, said at least one recessed area extending substantially into said surface; and
   (c) said flange having first and second recessed areas along each side of said second pair of sides, said first and second recessed areas extending substantially to said surface, and said flange having a third recessed area between said first and second recessed areas, said third recessed area extending toward said surface but not extending as far as said first and second recessed areas.

2. The lid of claim 1, wherein said flange along each side of said first pair of sides comprises at least two said recessed areas.

3. The lid of claim 1, wherein said third recessed area extends toward said surface about half the depth of said flange.

4. The lid of claim 1 wherein said first, second and third recessed areas are contiguous.

5. The lid of claim 4, wherein said third recessed area has a substantially straight leading edge.

6. The lid of claim 1, sized to operatively cover a microplate meeting standard MP96-3.

7. The lid of claim 1, further comprising a sealing feature for sealing to the top of a microplate, said sealing feature comprising a substantially continuous lip depending from the lower surface of the lid slightly inboard of said first and said second pairs of sides of the rectangular surface and uninterrupted by any recesses.

* * * * *